US011207076B2

(12) United States Patent
Clark

(10) Patent No.: US 11,207,076 B2
(45) Date of Patent: Dec. 28, 2021

(54) LOCKING MECHANISM FOR HEMOSTASIS DEVICE

(71) Applicant: FORGE MEDICAL, INC., Philadelphia, PA (US)

(72) Inventor: Timothy W. I. Clark, Philadelphia, PA (US)

(73) Assignee: FORGE MEDICAL, INC., Philadelphia, PA (US)

( * ) Notice: Subject to any disclaimer, the term of this patent is extended or adjusted under 35 U.S.C. 154(b) by 261 days.

(21) Appl. No.: 16/356,368

(22) Filed: Mar. 18, 2019

(65) Prior Publication Data

US 2019/0314027 A1    Oct. 17, 2019

Related U.S. Application Data

(60) Provisional application No. 62/644,212, filed on Mar. 16, 2018.

(51) Int. Cl.
*A61B 17/128* (2006.01)
*A61B 17/122* (2006.01)
*A61B 17/12* (2006.01)

(52) U.S. Cl.
CPC .......... *A61B 17/128* (2013.01); *A61B 17/122* (2013.01); *A61B 2017/12004* (2013.01)

(58) Field of Classification Search
CPC ................ A61B 17/12; A61B 17/0057; A61B 2017/12004; A61B 5/022; A61B 5/02233
USPC ................................................. 606/201–203
See application file for complete search history.

(56) References Cited

U.S. PATENT DOCUMENTS

| 3,086,530 | A | 4/1963 | Groom |
| 5,263,965 | A | 11/1993 | Roth |
| 5,304,201 | A | * | 4/1994 | Rice ..................... A61B 17/132 606/151 |
| 5,728,120 | A | 3/1998 | Shani et al. |
| 6,068,646 | A | 5/2000 | Lam |
| 6,316,686 | B1 | 11/2001 | Byrd |
| 6,332,879 | B1 | 12/2001 | Nielsen |
| 7,780,612 | B2 | 8/2010 | Ross |
| 8,788,982 | B2 | * | 7/2014 | Lippincott ............ G06F 30/398 716/53 |
| 2002/0058893 | A1 | 5/2002 | Vesey |
| 2003/0028214 | A1 | 2/2003 | Benz et al. |
| 2004/0068290 | A1 | 4/2004 | Bates et al. |
| 2008/0269659 | A1 | 10/2008 | Bergin |

(Continued)

FOREIGN PATENT DOCUMENTS

EP    0067622 A1    12/1982

*Primary Examiner* — Tuan V Nguyen
(74) *Attorney, Agent, or Firm* — Moore & Van Allen PLLC

(57) ABSTRACT

An accessory for a VasoStat™ hemostasis device that locks the plunger within the cylinder through which the plunger travels by restricting disengagement of ratcheted wings affixed to the plunger. The accessory may be repositioned or removed so that the ratcheted wings may be disengaged and the plunger may be retracted within the cylinder. When integrated into the plunger, the accessory may be configured to move between a first unlocked position and a second locked position. As a separate component, the accessory is configured to be positioned over and locked into position on the hemostasis device, such as the central stem of the plunger.

14 Claims, 7 Drawing Sheets

(56) References Cited

U.S. PATENT DOCUMENTS

| | | |
|---|---|---|
| 2009/0171192 A1 | 7/2009 | Patrick et al. |
| 2009/0281565 A1 | 11/2009 | McNeese |
| 2010/0152770 A1 | 6/2010 | Spencer |
| 2010/0217202 A1 | 8/2010 | Clark |
| 2010/0280541 A1* | 11/2010 | Lampropoulos ..... A61B 17/132 606/203 |
| 2011/0196417 A1 | 8/2011 | Clark |
| 2013/0237943 A1 | 9/2013 | Erland |

* cited by examiner

LOCKING MECHANISM FOR HEMOSTASIS DEVICE

FIELD OF THE INVENTION

The present disclosure relates to locking mechanisms for devices that adhere to a patient's skin at a vascular access site and apply a compressive force to the puncture site to achieve hemostasis, and particularly to mechanisms used for releasably locking hemostasis devices while applying hemostatic compression to a patient.

BACKGROUND

There are many devices and procedures currently employed in the medical field for achieving hemostasis at a percutaneous vascular access site resulting, for example, from a transradial cardiac catheterization procedure.

Among such prior art devices and procedures are, for example: a non-woven sponge manually applied directly to the site of the bleeding at the puncture site; band-type devices tightened around the arm of the patient and possessing an inflatable balloon over the blood vessel; and notch-shaped compression pad tightened around the arm of the patient much like an electrical tie.

Each of these prior art devices and procedures requires extensive interaction with a patient by a clinician. For example, a non-woven sponge requires the clinician apply pressure to the puncture site until hemostasis is achieved. Similarly, band-shaped compression device requires the clinician to use both hands to wrap the device around the arm (or leg) or a patient and inflate the compressive balloon using an air-filled syringe such that the pressure is applied appropriately to the puncture site. None of these prior art devices provides the clinician with a device that can be applied with a single hand in a manner that allows the clinician to simultaneously remove the vascular access sheath so that hemostasis is achieved.

Improving on these prior art devices and procedures, the VasoStat™ hemostasis device has been developed. The VasoStat™ hemostasis device is configured to apply a compressive force to a patient's skin at the site of a percutaneous vascular access. This device comprises a footplate, a cylinder positioned on the footplate, a plunger positioned within the cylinder and configured to move therethrough, and motion restricting means interposed between the cylinder and the plunger, the motion restricting means configured such that as the plunger moves toward the skin movement of the plunger away from the skin is restricted until the restricting means are released. So configured, this hemostasis device permits single-handed operation allowing the clinician to quickly and efficiently apply the hemostasis device to the puncture site.

The VasoStat™ hemostasis device employs ratcheted wings to restrict movement of the plunger away from the skin of the patient. In operation, these ratcheted wings secure the plunger to the patient's skin in order to maintain hemostatic compression. When hemostasis has been achieved, the compressive force may be released by the inward movement of the ratcheted wings which disengages the plunger from the cylinder. Disoriented or uncooperative patients, however, may seek to disengage the ratcheted wings and, in doing so, may prematurely release the compressive force. If the plunger of this hemostasis device were capable of being releasably locked, the risk of premature compression release by a disoriented or uncooperative patient could be reduced.

In applications in which the VasoStat™ hemostasis device is used to apply hemostatic compression to a vascular structures deeper from the skin than under usual conditions (such as, for example, for a morbidly obese patient with a radial artery located deeper from the skin surface, or a patient with a swollen lower leg in whom arterial access has been achieved deep to the skin surface), where the upward resistance imparted to the plunger surface by the greater force needed for compression, the fixation means locks the plunger in a position which prevents premature release of the device. Accordingly, there is a need for locking mechanisms for such hemostasis devices.

SUMMARY OF THE INVENTION

A locking mechanism for hemostasis devices, such as the VasoStat™ hemostasis device, is provided. In one embodiment, the locking mechanism comprises an elongated tab rotatably affixed to the top of the plunger by means of a pin. The tab is configured to be rotated 90° about the pin between a first, unlocked position, and a second, locked position. With the plunger depressed and the ratcheted wings engaged, the locking mechanism in rotated from the first position to the second position, thereby restricting the inward movement and disengagement of the ratcheted wings.

In another embodiment, the locking mechanism may comprise a compressible member affixed to the top of the plunger and configured to be movable between a first, uncompressed and unlocked position, and a second, compressed and locked position. With the plunger depressed and the ratcheted wings engaged, the compressible member in compressed from the first (disengaged) position into the second (engaged) position, in which the inward movement and disengagement of the ratcheted wings is restricted.

In yet another embodiment, the locking mechanism may comprise a retaining bar pivotably connected to one of the ratcheted wings and configured to be releasably connected to the other ratcheted wing. With the plunger depressed and the ratcheted wings engaged, the retaining bar in pivoted from the first (disengaged) position into the second (engaged) position, thereby restricting the inward movement and disengagement of the ratcheted wings.

In still another embodiment, the locking mechanism may comprise a hinged member incorporated into the body or edge of the cylinder and configured to be releasably connected to the plunger. With the plunger depressed and the ratcheted wings engaged, the hinged member is rotated from a first (disengaged) position into the second (engaged) position, thereby restricting the inward movement and disengagement of the ratcheted wings.

In yet another embodiment, the locking mechanism may comprise a separate cylindrical element which may be positioned over and onto the hemostasis device, such as onto the central stem of the plunger. With the plunger depressed and the ratcheted wings engaged, the cylindrical element is lowered onto the plunger so that it restricts the inward movement and disengagement of the ratcheted wings.

BRIEF DESCRIPTION OF THE FIGURES

The invention is best understood from the following detailed description when read in connection with the accompanying drawings. The various features of the drawings may not be to scale. Included in the drawings are the following figures.

DETAILED DESCRIPTION

Figure 1:
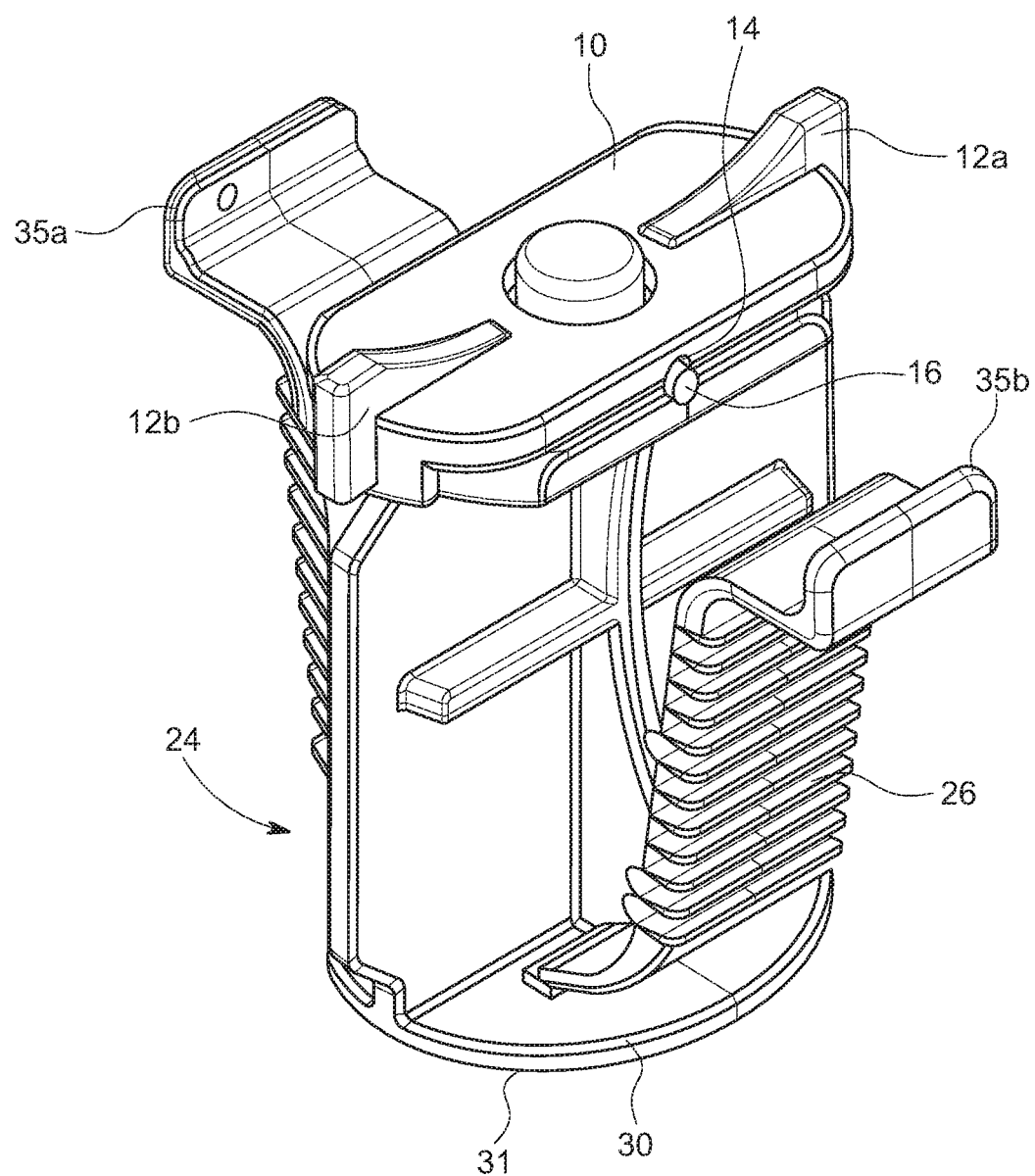
FIG. 1 is a perspective view of an exemplary embodiment of a locking mechanism affixed to the plunger of a VasoStat™ hemostasis device.
Figure 2:
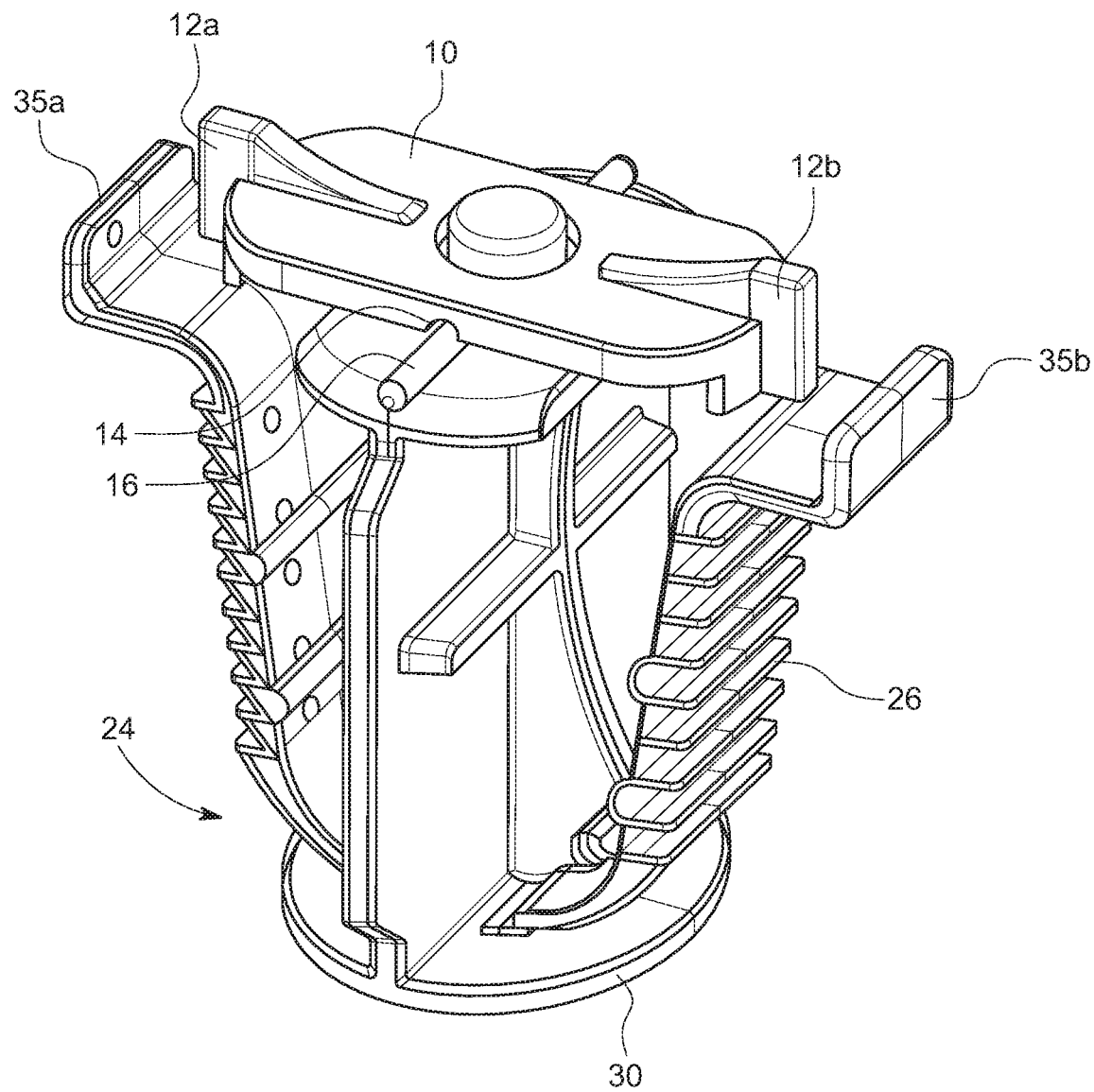
FIG. 2 is a perspective view of the locking mechanism shown in FIGS. 1A-1C in which the locking mechanism affixed to the plunger of a VasoStat™ hemostasis device has been rotated into a locked position.
Figure 3A:
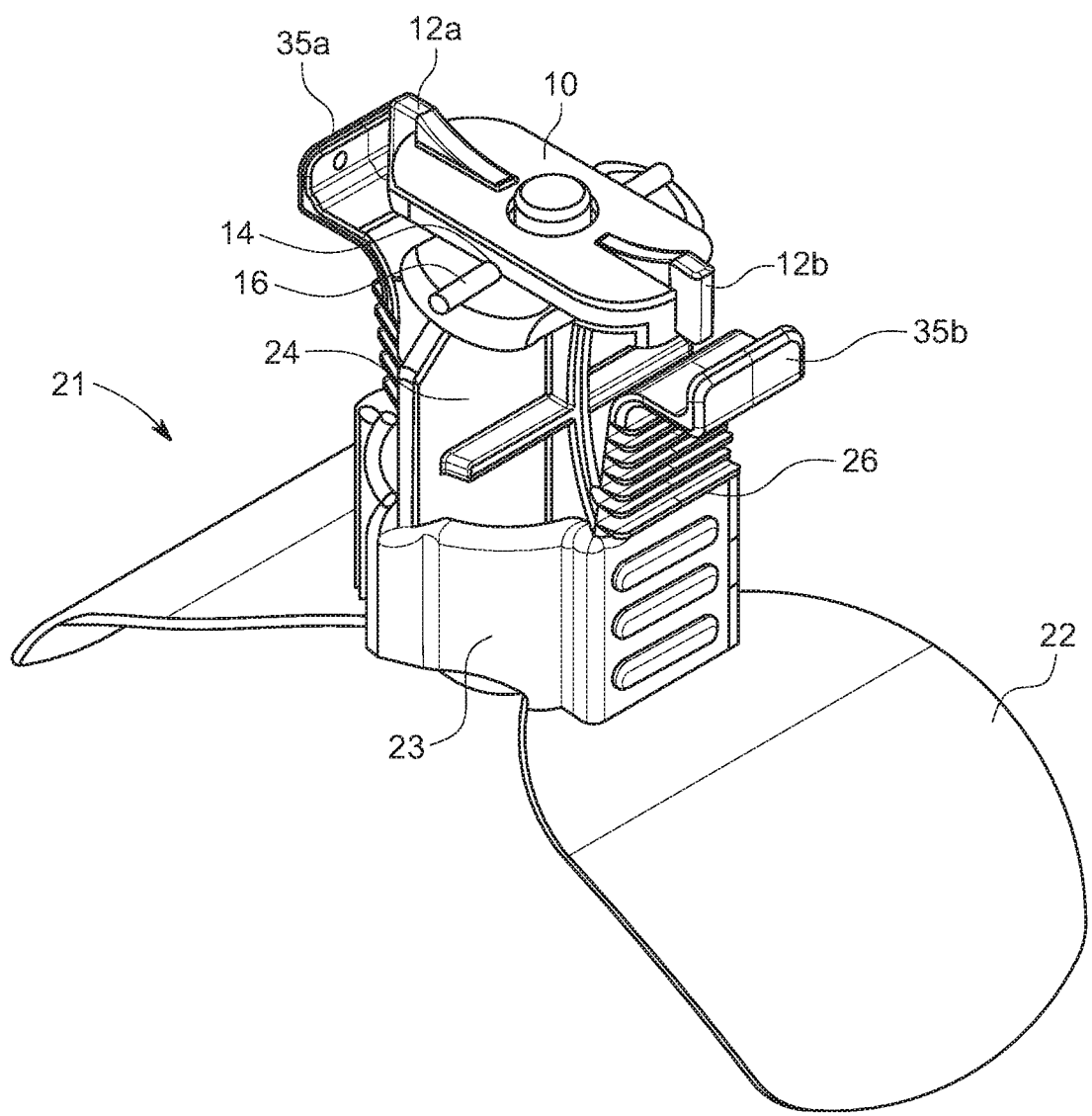
FIG. 3A is a perspective view of a VasoStat™ hemostasis device in which the locking mechanism shown in FIGS. 1A-1C has been rotated into a locked position.
Figure 3B:
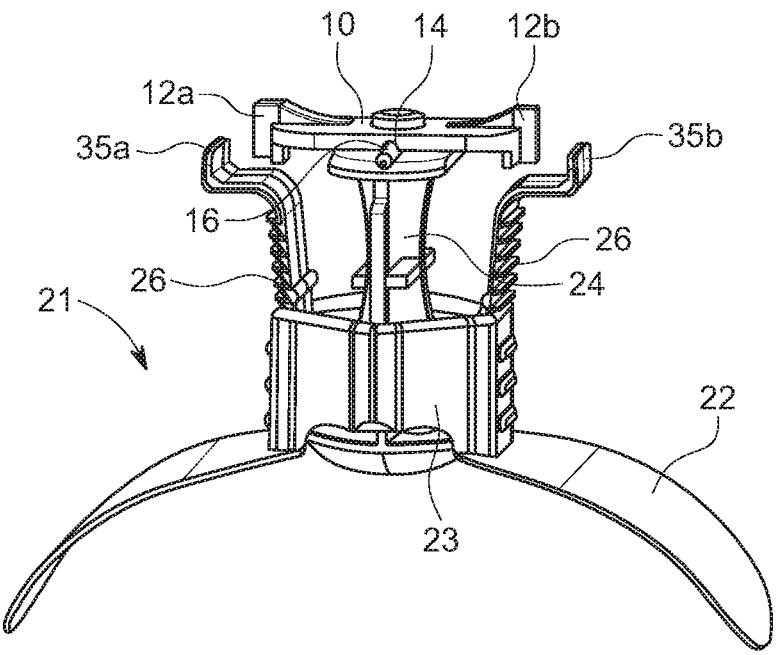
FIG. 3B is another perspective view of a VasoStat™ hemostasis device in which the locking mechanism shown in FIGS. 1A-1C has been rotated into a locked position.
Figure 3C:
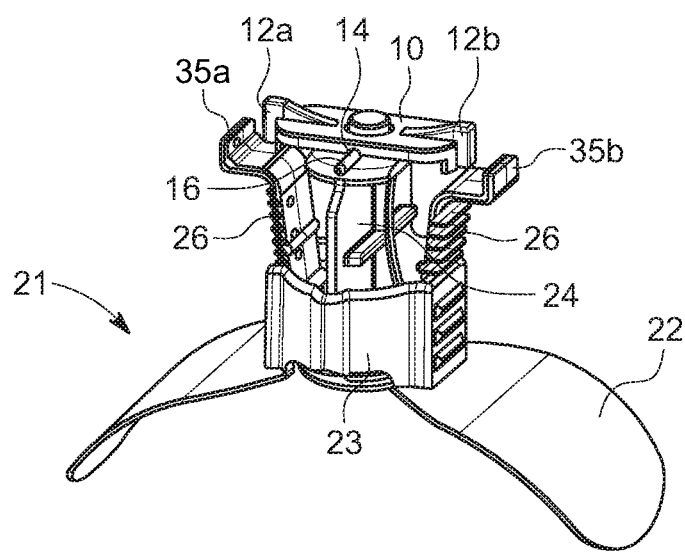
FIG. 3C is yet another perspective view of a VasoStat™ hemostasis device in which the locking mechanism shown in FIGS. 1A-1C has been rotated into a locked position.

As shown in the embodiment illustrated in FIGS. 1A-1C, 2A, 2B, 3A-3D, and 4A-4E, the locking mechanism comprises an elongated tab 10 rotatably affixed to the top of the plunger 24 of a VasoStat™ hemostasis device. The elongated tab 10 may be affixed by means of a pin, a locking snap fastener, or other such suitable connector (not shown), and is configured to be rotatable between a first, unlocked position, and a second, locked position. In the first, unlocked position, as shown in FIGS. 1A-1C, the ratcheted wings 35a and 35b attached to the base of the plunger 24 are not restricted in their inward movement. When rotated into the second, locked position, as shown in FIGS. 2A, 2B, and 3A-3D, the elongated tab 10 is oriented such that the top ends of the ratcheted wings 35a and 35b are restricted from inward movement. So restricted, the plunger 24 cannot be disengaged and the compressive force is maintained.

Figure 4A:
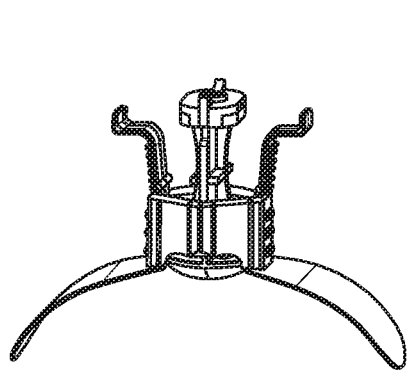
FIG. 4A is a side perspective view of a VasoStat™ hemostasis device in which the locking mechanism shown in FIGS. 1A-1C is in the unlocked position.
Figure 4B:
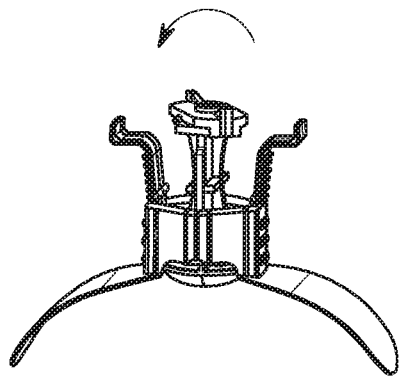
FIG. 4B is a side perspective view of a VasoStat™ hemostasis device in which the locking mechanism shown in FIGS. 1A-1C has been rotated from the unlocked position.
Figure 4C:
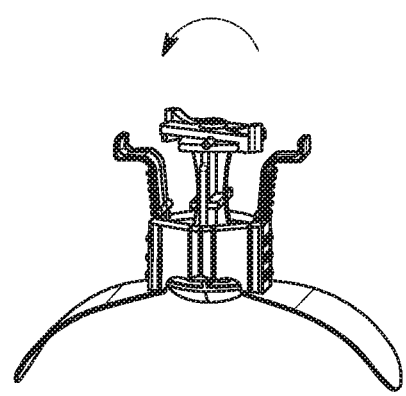
FIG. 4C is a side perspective view of a VasoStat™ hemostasis device in which the locking mechanism shown in FIGS. 1A-1C has been rotated halfway between the unlocked position and the locked position.
Figure 4D:
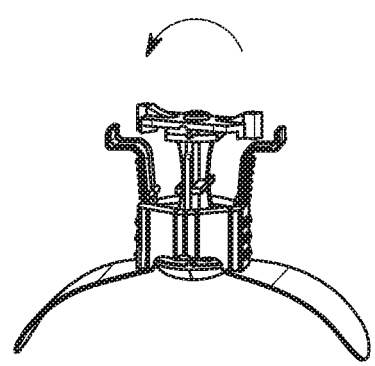
FIG. 4D is a side perspective view of a VasoStat™ hemostasis device in which the locking mechanism shown in FIGS. 1A-1C has been rotated close to the locked position.
Figure 4E:
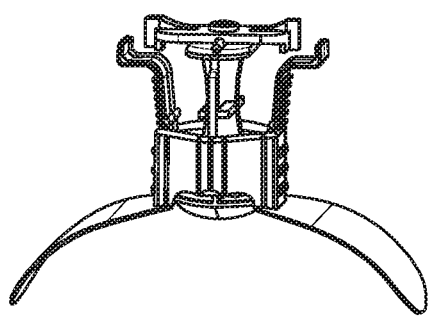
FIG. 4E is a side perspective view of a VasoStat™ hemostasis device in which the locking mechanism shown in FIGS. 1A-1C has been rotated to the locked position.
Figure 5:
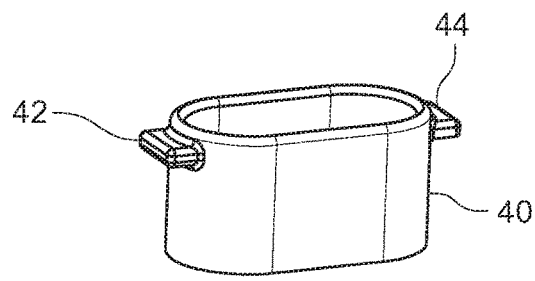
FIG. 5 is a perspective view of an alternate embodiment of a locking mechanism for a VasoStat™ hemostasis device.
Figure 6A:
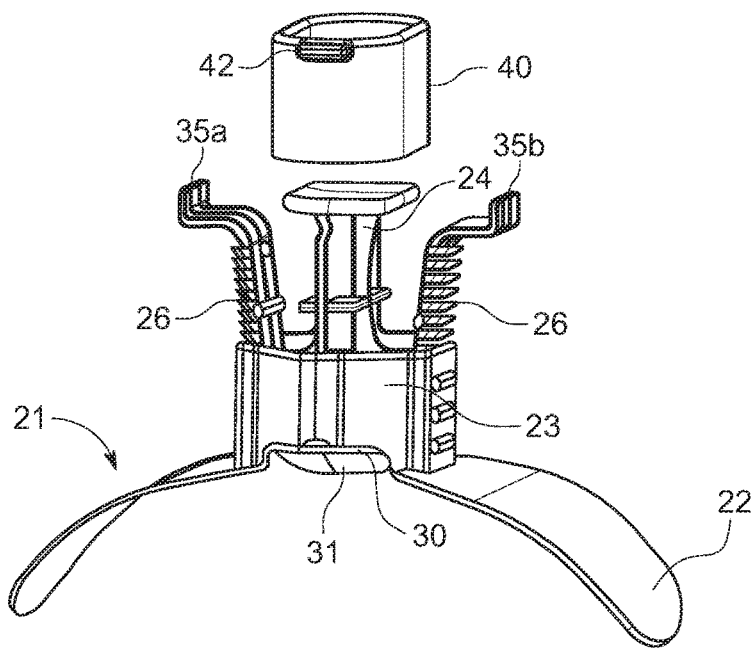
FIG. 6A is a perspective view of the locking mechanism shown in FIG. 5 positioned over the plunger of a VasoStat™ hemostasis device.
Figure 6B:
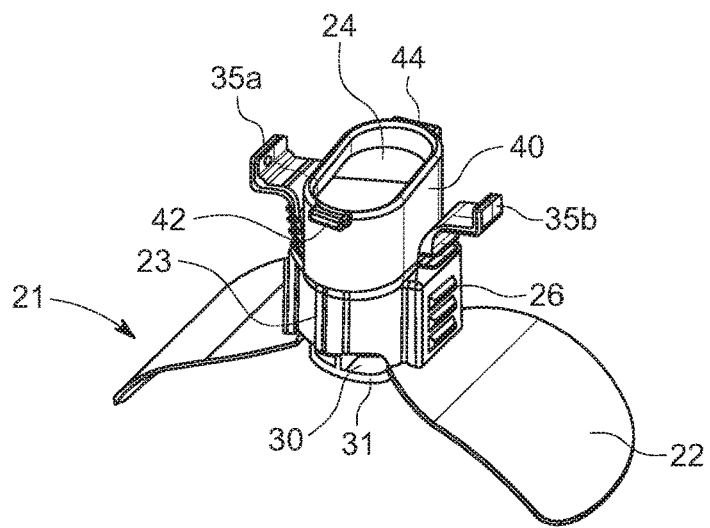
FIG. 6B is a perspective view of a VasoStat™ hemostasis device in which the locking mechanism shown in FIG. 5 has been positioned on the plunger.

FIGS. 4A-4E show the progression of rotation of the elongated tab 10 from in the unlocked position (shown in FIG. 4A) to the locked position (shown in FIG. 4E) as well as three intermediate positions (shown in FIGS. 4B-4D). As depicted, the elongated tab 10 is rotated 90° between the unlocked and locked positions. In operation, the VasoStat™ hemostasis device is applied to the patient with the locking mechanism in the unlocked position. Once affixed to the patient, the locking mechanism may be engaged and maintained in place for the duration of application. When applied to disoriented or uncooperative patients, the locking mechanism for the VasoStat™ hemostasis device reduces the risk of premature release of compression. Once hemostasis has been achieved, the locking mechanism may be disengaged so that the compressive force is removed.

The elongated tab may be provided with one or more raised portions 12a and 12b to facilitate gripping in rotational movement. The underside of the elongated tab may also be provided with a groove or ridge 14 that mates with a corresponding structure 16 on the top surface of the plunger to provide haptic or auditory feedback indicating the proper rotation of the tab into the locked position.

As shown in the embodiment illustrated in FIGS. 5 and 6A-6D, the locking mechanism comprises a separate cylindrical element 40 which may be positioned over and onto the central stem of the plunger 24 of a VasoStat™ hemostasis device 21. With the plunger 24 depressed and the ratcheted wings 35a and 35b engaged, the cylindrical element 40 is positioned onto the central stem of the plunger 24 so that the inward movement and disengagement of the ratcheted wings 35a and 35b is restricted. The cylindrical element 40 may have one or more flanges 42 and 44 extending outward from the top edge of the cylinder 40. These flanges 42 and 44 more readily permit a firm grip on the cylindrical element 40 when placing it onto and removing it from central stem of the plunger 24 of a VasoStat™ hemostasis device 21. The top of the cylindrical element 40 may be open or, alternatively, it may be enclosed. If open, the top surface of the plunger 24 would be visible. And if enclosed, the cylindrical element 40 forms an inverted, elongated cup that is placed over the top end of the plunger 24.

In embodiments with an open cylindrical element, the outer wall of the cylindrical element 40 and/or the top surface of the plunger 24 may be configured to permit the placement of written indicia of the time of application of the hemostasis device. In embodiments with a closed cylindrical element, the outer wall and/or the top surface of the cylindrical element 40 may be configured to permit the placement of written indicia of the time of application of the hemostasis device.

Figure 7:
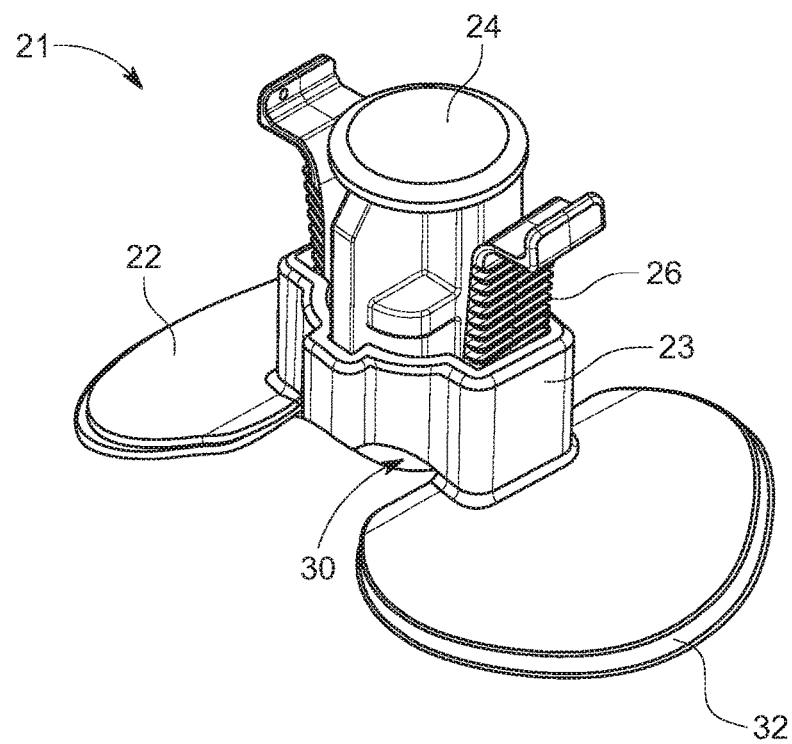
FIG. 7 illustrates an exemplary embodiment of a VasoStat™ hemostasis device for use with a locking mechanism according to the present invention.
Figure 8:
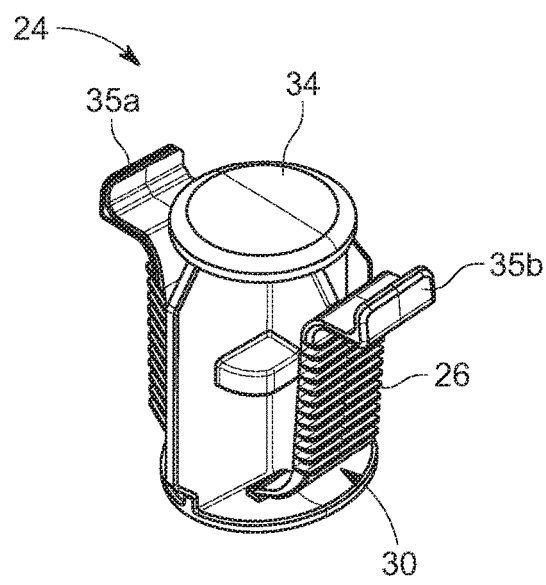
FIG. 8 is a perspective view of an exemplary plunger for use in the hemostasis device of FIG. 7.
Figure 9:
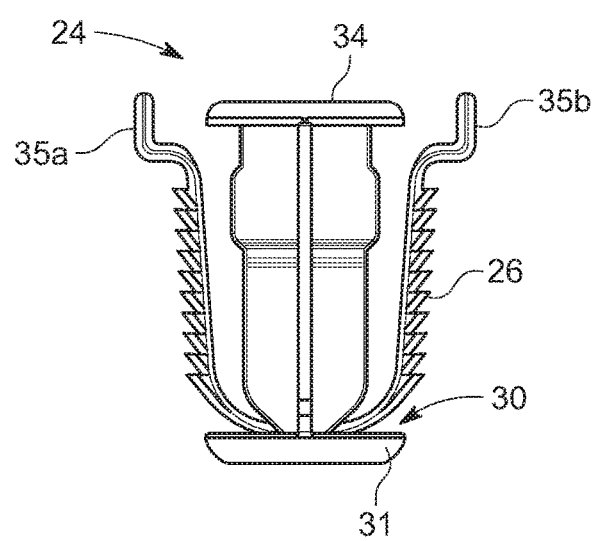
FIG. 9 is a side view of an exemplary plunger for use in the hemostasis device of FIG. 7.

Exemplary hemostasis devices suitable for use with the adhesive pad of the present invention are shown in FIGS. 7-9. The hemostasis device 21 may comprise a footplate 22, a cylinder 23 centrally positioned on footplate 22, and a plunger 24. The engagement of the plunger 24 within the cylinder 23 provides for one-directional movement of the plunger 24 with respect to the cylinder 23 by use of a ratcheting mechanism. In the embodiment shown in FIGS. 7-9, a plurality of racks 26 attached to the plunger 24 may engage a corresponding pawl or rack (not shown) in the cylinder 23 in such manner as to limit the plunger 24 to movement downwardly in the cylinder 23. In other words, the plunger 24 may be forced downwardly toward the puncture site, but is restrained from movement upwardly in the cylinder 23 by the combination and position of racks 26 and the corresponding pawls or racks in the cylinder 23. In another embodiment, a single rack 26 is attached to the plunger 24 and may engage a corresponding pawl or rack in the cylinder 23. In yet another embodiment, one or more racks 26 positioned on the cylinder 23 may engage a pawl positioned on plunger 24 in such manner as to limit plunger 24 to movement downwardly in cylinder 23.

As shown in FIGS. 8 and 9, the plunger 24 may include various components. For example, the plunger 24 may be designed and configured such that the plunger includes a central plunger portion 34 and wings 35a and 35b. The central plunger portion 34 may be configured to receive applied downward force as provided by the clinician. The wings 35a and 35b may include the racks 26 such that as the clinician applies force to the central plunger portion 34, the wings 35a and 35b ratchet downward against the racks 26 of the cylinder 23. The wings 35a and 35b may also provide a means for releasing the pressure being applied to the puncture site by the plunger 24. The wings 35a and 35b may be squeezed toward the central plunger portion 34, thereby disengaging the racks 26, allowing the plunger 24 to move away from the puncture site. This may be done when hemostasis is achieved or if too much pressure has been applied to the puncture site. Further, this embodiment permits one-handed movement of the plunger 24 from the puncture site by compression of wings 35a and 35b and movement of the plunger 24 through the cylinder 23 and away from the puncture site.

Similarly, the bottom of the plunger 24 may include a compression surface 30 having a compression pad 31 adhered thereto. The compression pad 31 may have a pro-coagulant coating such as calcium alginate, oxidized regenerated cellulose, seaweed extracts, a pro-coagulant polymer, another pro-coagulant coating, or combinations of two or more of these. The compression pad 31 may also have an antimicrobial coating such as silver or chlorhexidine.

One or more adhesive pads 32 having adhesive surfaces may be applied to the bottom of the footplate 22 such that, during operation, the pads 32 may adhere to the skin of the patient when the hemostasis device 21 is in use, thereby assisting in securing the footplate 22 to the patient's skin to prevent the hemostasis device from shifting position on the skin when in use. The size of the pads 32 may be determined relative to the pressure being applied by the hemostasis device 21 to the puncture site and/or the part of the body to which the hemostasis device 21 is being applied. The size of the pads may also be determined relative to the type of adhesive being used on the pads. For example, the pulling force exerted on the patient's skin by the one or more pads 32 should be greater than the compressive force applied on the puncture site by the plunger 24. Higher compressive forces applied on the puncture site may be achieved by increasing the surface area of the pads 32 that are in contact with the skin, either by increasing the size and/or number of pads 32, using an adhesive having greater adhesive strength, or a combination of the two. Typical temporary medical adhesives may be used such that when hemostasis is achieved, the hemostasis device 21 is easily removed.

It should be noted that the hemostasis device as shown in FIGS. 7-9 is shown by way of example only. Additional design features may be incorporated. For example, although only a ratcheting mechanism is disclosed herein to permit only unidirectional movement of plunger, additional locking mechanisms such as a screw machine (not shown herein) or other similar mechanisms may be employed.

The method for applying a compressive force to a patient's skin at a puncture site using the hemostasis devices as shown in FIGS. 7-9 will now be described. The hemostasis device 21 is placed on the skin of a patient about a puncture site and adhered to the skin via one or more adhesive pads 32. The plunger 24 is then pressed downward through the cylinder 23 toward the puncture site until appropriate pressure has been applied to the puncture site by the compression pad 31. The hemostasis device 21 is then left in position, thereby allowing the medical technician operating the device to perform other tasks until hemostasis is achieved.

It should be noted that the configurations and mechanisms discussed above are shown by way of example only. Additional configurations and mechanisms may be used to implement a hemostasis system. For example, a compressive force may be applied directly to the footplate. As above, the footplate may be adhered directly to a patient's skin proximal a puncture site. An inflatable bladder or other mechanical expander may be positioned between the footplate and the puncture site or between the footplate and a second plate positioned on the side of the footplate distal to the puncture site and attached to the footplate only at each end such that the bladder is positioned between the footplate and the second plate. The bladder or other mechanical expander may then be inflated, exerting a force against the footplate and thus providing a compressive force against the puncture site. Once hemostasis is achieved, the bladder or other mechanical expander may be deactivated and the footplate removed from the patient's skin. Examples of alternative mechanical expanders that may also be used include spring-loaded and threaded expanding devices.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments. Thus, this disclosure is not limited to the particular systems, devices, and methods described, as these may vary.

The terminology used in the description is for the purpose of describing the particular versions or embodiments only, and is not intended to limit the scope. As used in this document, the singular forms "a," "an," and "the" include plural references unless the context clearly dictates otherwise. Unless defined otherwise, all terms used herein have the same meanings as commonly understood by one of ordinary skill in the art.

As various changes could be made in the above articles and methods without departing from the scope of the invention, it is intended that all matter contained in the above description shall be interpreted as illustrative and not in a limiting sense. Other embodiments within the scope of the claims herein will be apparent to one skilled in the art from consideration of the specification or practice of the invention as disclosed herein. It is intended that the specification be considered exemplary only, with the scope and spirit of the invention being indicated by the claims. The appended claims are intended to be construed to include all such embodiments and equivalent variations.

I claim:

1. A locking hemostasis device for adhering to a patient's skin and applying a compressive force to a puncture site, the device comprising:
   a footplate
   a receiving device positioned on the footplate,
   a plunger a top surface wherein the plunger is positioned within the receiving device and configured to move therethrough and apply a compressive force to the patient's skin at the puncture site, a plurality of motion restricting components interposed between the receiving device and the plunger to restrict reverse movement of the plunger through the receiving device; and an elongated tab having a long axis, a top surface, and a bottom surface, wherein the elongated tab is rotatably affixed to the top surface of the plunger and configured to be rotatable between a first unlocked position in which the plurality of motion restricting components are unrestricted from inward movement and a second locked position in which the plurality of motion restricting components are restricted from inward movement.

2. The locking hemostasis device of claim 1, wherein the bottom surface of the elongated tab is provided with a groove.

3. The locking hemostasis device of claim 2, wherein the top surface of the plunger is provided with a ridge configured to mate with the groove disposed on the bottom surface of the elongated tab.

4. The locking hemostasis device of claim 3, wherein the ridge disposed on the top surface of the plunger is configured to mate with the groove disposed on the bottom surface of the elongated tab when the elongated tab is rotated into the locked position.

5. The locking hemostasis device of claim 2, wherein the groove disposed on the bottom surface of the elongated tab bisects the bottom surface transverse to the long axis of the elongated tab.

6. The locking hemostasis device of claim 1, wherein the bottom surface of the elongated tab is provided with a ridge.

7. The locking hemostasis device of claim 6, wherein the top surface of the plunger is provided with a groove configured to mate with the ridge disposed on the bottom surface of the elongated tab.

8. The locking hemostasis device of claim 7, wherein the groove disposed on the top surface of the plunger is configured to mate with the ridge disposed on the bottom surface of the elongated tab when the elongated tab is rotated into in the locked position.

9. The locking hemostasis device of claim 6, wherein the ridge disposed on the bottom surface of the elongated tab bisects the bottom surface transverse to the long axis of the elongated tab.

10. The locking hemostasis device of claim 1, wherein the top surface of the elongated tab is provided one or more raised portions configured to facilitate gripping when the elongated tab is rotated.

11. A method for applying a locked compressive force to a patient's skin at the site of a puncture site, the method comprising the steps of:

placing a hemostasis device on the patient's skin at the site of a puncture site, wherein the hemostasis device comprises a footplate, a receiving device positioned on the footplate, a plunger positioned within the receiving device and configured to move therethrough, a plurality of motion restricting components interposed between the receiving device and the plunger to restrict reverse movement of the plunger through the receiving device, and an elongated tab having a top surface and a bottom surface, wherein the elongated tab is rotatably affixed to the top surface of the plunger and configured to be rotatable between a first unlocked position in which the plurality of motion restricting components are unrestricted from inward movement and a second locked position in which the plurality of motion restricting components are restricted from inward movement;

advancing the plunger through the receiving device until the plunger applies a compressive force to the puncture site;

engaging the plurality of motion restricting components to restrict reverse movement of the plunger through the receiving device; and rotating the elongated tab from the first unlocked position to the second locked position.

12. The method of claim 11, wherein the top surface of the plunger is provided with a ridge configured to mate with a groove disposed on the bottom surface of the elongated tab when the elongated tab is rotated into the locked position.

13. The method of claim 11, wherein the top surface of the plunger is provided with a groove configured to mate with a ridge disposed on the bottom surface of the elongated tab when the elongated tab is rotated into the locked position.

14. The method of claim 11, wherein the top surface of the elongated tab is provided one or more raised portions configured to facilitate gripping when the elongated tab is rotated.

* * * * *

UNITED STATES PATENT AND TRADEMARK OFFICE
CERTIFICATE OF CORRECTION

| | |
|---|---|
| PATENT NO. | : 11,207,076 B2 |
| APPLICATION NO. | : 16/356368 |
| DATED | : December 28, 2021 |
| INVENTOR(S) | : Timothy W. I. Clark |

It is certified that error appears in the above-identified patent and that said Letters Patent is hereby corrected as shown below:

In the Claims

In Column 6, Claim 1, please change Line 64 to:
a plunger having a top surface wherein the plunger is positioned Signed and Sealed this
Third Day of May, 2022

*Katherine Kelly Vidal*

Katherine Kelly Vidal
*Director of the United States Patent and Trademark Office*